(12) United States Patent
Callison et al.

(10) Patent No.: US 8,920,849 B1
(45) Date of Patent: Dec. 30, 2014

(54) SKIN TREATMENT METHOD AND SYSTEM

(76) Inventors: Kenneth P. Callison, Lonetree, CO (US); Nelson McNulty, Edgewater, CO (US)

(*) Notice: Subject to any disclaimer, the term of this patent is extended or adjusted under 35 U.S.C. 154(b) by 2103 days.

(21) Appl. No.: 11/725,644

(22) Filed: Mar. 19, 2007

Related U.S. Application Data

(60) Provisional application No. 60/787,406, filed on Mar. 30, 2006.

(51) Int. Cl.
- *A61K 33/00* (2006.01)
- *A61K 33/14* (2006.01)
- *A61M 11/00* (2006.01)
- *A61P 17/00* (2006.01)

(52) U.S. Cl.
USPC ... 424/613; 424/680; 128/200.14; 250/423 R; 250/424; 604/290; 604/310

(58) Field of Classification Search
None
See application file for complete search history.

(56) References Cited

U.S. PATENT DOCUMENTS

| | | | |
|---|---|---|---|
| 2,284,235 A * | 5/1942 | Ronzi | 128/200.14 |
| 3,990,452 A * | 11/1976 | Murry et al. | 606/169 |
| 4,686,370 A * | 8/1987 | Blach | 250/423 R |
| 4,776,515 A | 10/1988 | Michalchik | |
| 5,494,674 A | 2/1996 | Barnett et al. | |
| 5,785,521 A | 7/1998 | Rizoiu et al. | |
| 5,866,082 A | 2/1999 | Hatton et al. | |
| 6,149,620 A | 11/2000 | Baker et al. | |
| 6,478,754 B1 * | 11/2002 | Babaev | 601/2 |
| 6,719,754 B2 | 4/2004 | Underwood et al. | |
| 2001/0032001 A1 | 10/2001 | Ricart et al. | |
| 2003/0028189 A1 | 2/2003 | Woloszko et al. | |
| 2004/0234618 A1 | 11/2004 | Saito | |

FOREIGN PATENT DOCUMENTS

JP 404243899 8/1992

OTHER PUBLICATIONS

Krueger, The biological effects of air ions, Int. J. Biometeor. (1985), vol. 29, No. 3, pp. 205, 206.*

* cited by examiner

*Primary Examiner* — Abigail Fisher
*Assistant Examiner* — Frank Choi
(74) *Attorney, Agent, or Firm* — Kenneth P. Callison

(57) ABSTRACT

A skin treatment method which includes ionizing oxygen and then mixing the ionized oxygen with saline solution to produce an energized saline solution is disclosed. The method further includes applying the energized saline solution to the skin as a mist-like spray to treat the skin. The system used to carry out the method includes an oxygen concentrator for generating oxygen and an ionizer for imparting an electric charge to the oxygen to produce ionized oxygen. The system also includes a bag of saline solution as well as a peristaltic pump for pumping the saline solution from the bag to a spray nozzle mounted in a handheld wand. The concentrator further includes apparatus for pumping or delivering the oxygen and ultimately the ionized oxygen to the spray nozzle. The spray nozzle mixes and atomizes the ionized oxygen and saline solution to produce a spray-like mist of the same which is then applied to an individual's skin.

6 Claims, 3 Drawing Sheets

SKIN TREATMENT METHOD AND SYSTEM

CROSS REFERENCE TO RELATED APPLICATIONS

This application is a nonprovisional application claiming the benefit under 35 USC 119(e) of U.S. provisional application Ser. No. 60/787,406, filed on Mar. 30, 2006.

TECHNICAL FIELD OF THE INVENTION

The invention pertains generally to methods and systems for treating the skin and, more particularly, to methods and systems for treating skin without traumatizing the tissue.

BACKGROUND OF THE INVENTION

Mens' and womens' desire to improve the appearance of their skin is relentless—as demonstrated by the fact that one cannot watch television very long today without viewing a commercial advertising some sort of product for controlling acne or eliminating skin lines caused by aging or the effects of too much exposure to the sun.

Almost all of these commercials claim that their particular product or treatment is superior to others on the market. Some commercials claim that the use of their products or treatments will not traumatize the skin in any way. Other than moisturizers, as a general rule, this is not the case. For example, many acne creams or alpha hydroxy acids cause the skin to dry out or peel. In addition, micro-dermabrasion treatments often traumatize the skin, dehydrate the face, and produce uneven results. Microdermabrasion propels aluminum oxide crystals at a high speed directly across the surface of the skin which often results in the crystals becoming imbedded into the tissue. Likewise, lasers and chemical peels damage the skin in order to stimulate collagen production. While use of some of these products and treatments may yield results, they do little to heal the tissue, and have various risks and side effects.

Thus, there remains a need and certainly a desire for products and treatments that will in fact treat various skin problems such as sun damaged or rough textured skin, aging or dehydrated skin, acne, rosacia, oily skin and scar tissue without traumatizing the skin.

DISCLOSURE OF THE INVENTION

The present invention addresses the aforementioned concerns by providing a method and system for treating an individual's skin plagued with any of the aforementioned problems without subjecting the individual to any substantial discomfort and without causing any trauma to the skin.

In its broadest sense, the method of the present invention includes ionizing a gas such as oxygen (although other gases such as nitrogen or even ambient air could be used) and then mixing the ionized gas with a desired liquid such as saline solution to produce an energized or ionized liquid or saline solution. The energized solution, preferably saline is then applied to the skin preferably in a mist-like spray form to treat the skin.

The preferred system or apparatus of the present invention used to carry out the aforementioned method includes a machine such as an oxygen concentrator for generating or delivering a desired gas such as oxygen. In addition, an ionizer is provided for imparting an electric charge to the desired gas to ionize the gas and thereby produce ionized gas. The system also preferably includes a reservoir for a desired liquid such as a bag of saline solution as well as a pump such as a peristaltic pump for delivering or pumping the saline solution or other desired liquid to a spray nozzle. The machine also preferably includes apparatus for pumping or delivering the desired gas and ultimately the ionized gas to the spray nozzle. The spray nozzle receives and mixes the ionized gas and desired liquid to produce a spray-like mist of energized solution comprising the ionized gas and desired liquid. The spray nozzle is incorporated within or attached to a handheld wand so that the spray-like ionized mist can be easily and conveniently applied to an individual's skin.

BRIEF DESCRIPTION OF THE DRAWINGS

The invention will be more readily understood by reference to the accompanying drawings wherein like reference numerals indicate like elements throughout the drawing figures, and in which.

DETAILED DESCRIPTION OF PREFERRED EMBODIMENT

Figure 1:
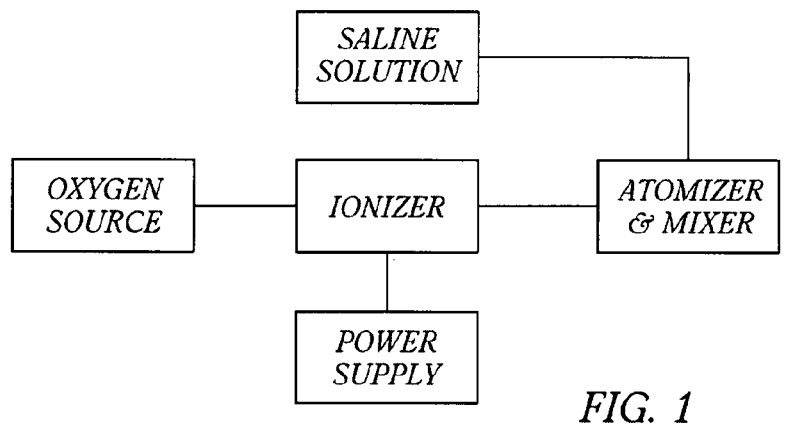
FIG. 1 is a flow chart of the method of the present invention.

As indicated in the foregoing disclosure of the invention, the present invention provides, inter alia, a method for treating skin suffering from a variety of problems such as acne, dryness, wrinkling due to aging etc. In its broadest sense and as shown in the flow chart of FIG. 1, the method includes ionizing a gas such as oxygen and then mixing the ionized gas with saline solution to produce energized saline solution. The energized or ionized solution is then applied to the skin preferably with a handheld wand 18 as shown in FIG. 2 to treat the skin.

Figure 4:
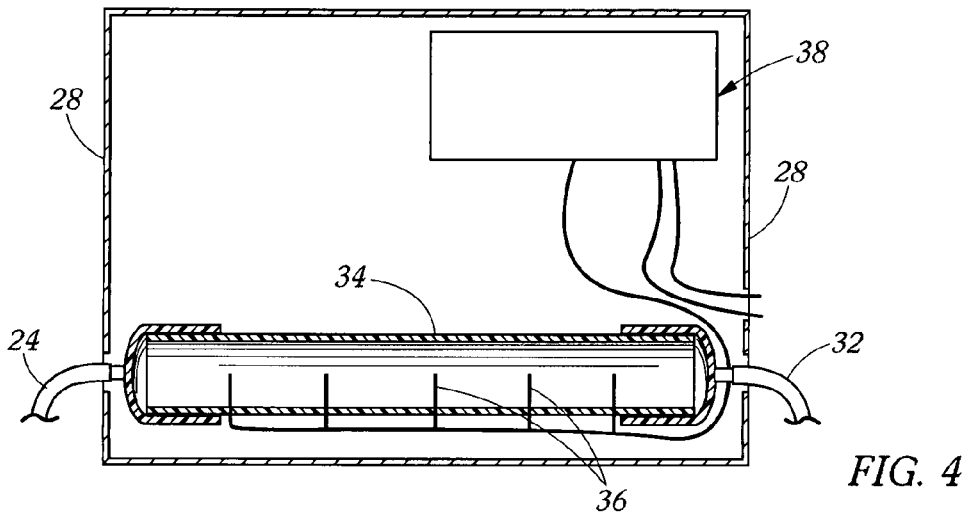
FIG. 4 is a cross sectional view taken along lines 4-4 of FIG. 3.
Figure 5:
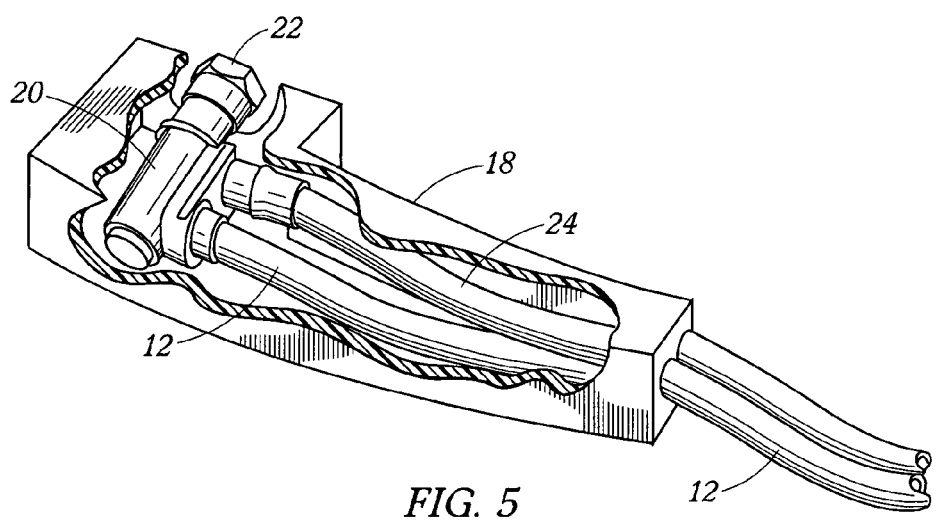
FIG. 5 is a partially broken away perspective view showing the inside components of the wand 18 shown in FIG. 2.
Figure 2:
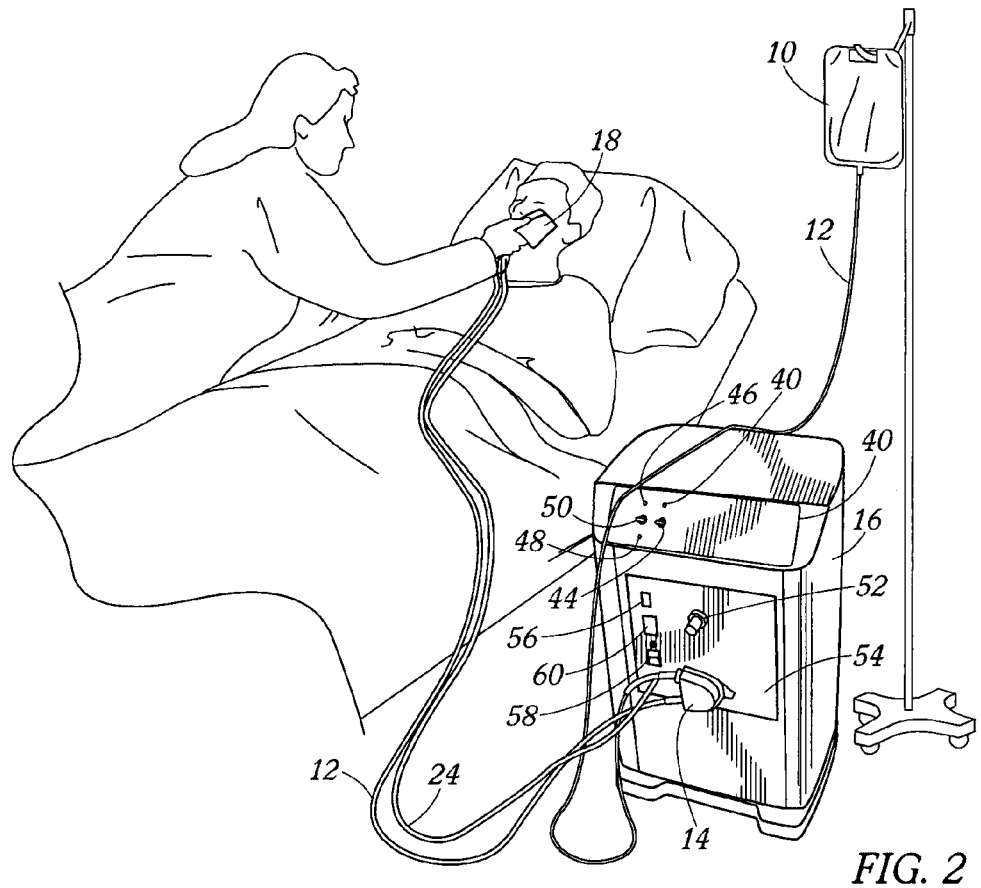
FIG. 2 is a perspective view showing the system of the present invention being used to apply an ionized mist produced by the system to the face of a patient to treat the patient's facial skin.

FIGS. 2-6 illustrate a preferred system for carrying out the method of the present invention on a patient. As shown in FIG. 2, saline solution in a bag 10 is drawn out or pumped from the bag via plastic tubing 12 by a peristaltic pump 14 which is attached to the front of an oxygen concentrator/ionizer machine 16. As also shown, tubing 12 extends through the peristaltic pump 14 which as shown in FIGS. 2 and 5 pumps or delivers the saline solution to a mixing chamber 20 of a spray nozzle 22 provided in wand 18. A persistaltic pump found to provide good results is available from Pulsafeeder, Inc. of Punta Gorda, Fla., Model No. Mec-O-Matic VSP-12.

Oxygen concentrator/ionizer machine 16 which generates ionized oxygen having either a negative or a positive charge, is also provided with tubing, i.e. tubing 24, which conveys the ionized oxygen generated by machine 16 to mixing chamber 20 of spray nozzle 22. The saline solution from tubing 12 mixes with the ionized oxygen from tubing 24 in the mixing chamber 20 of spray nozzle 22. The mixed solution is then preferably atomized as it passes through the nozzle so that it exits the nozzle as an ionized spray-like mist. The ionized mist is then applied directly to a patient's skin with wand 18 as shown in FIG. 2. A spray nozzle 22 found to produce an acceptable atomized mist of ionized or energized solution is made by the Wagner Spray Tech Corporation of Minneapolis, Minn., part number WAP0046457.

Figure 3:
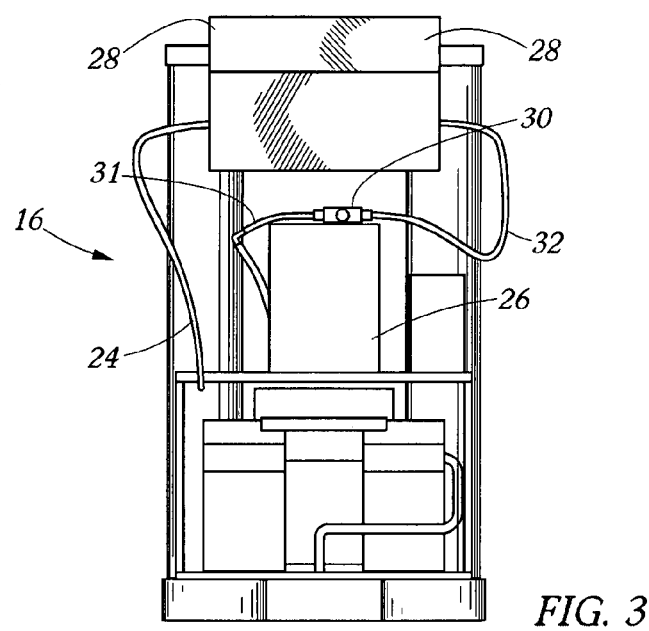
FIG. 3 is a front view showing machine 16 of FIG. 2 with its outer housing removed so as to show the machine's inner components.

Turning now to the oxygen concentrator/ionizer machine 16 shown in FIGS. 2-3, those skilled in the relevant art will appreciate that the machine includes an oxygen concentrator (not numbered) manufactured by the Airsep Corporation of Buffalo, N.Y., Model No. AS094-10 which is a concentrator of the type generating substantially pure oxygen. As illustrated in FIG. 3 which shows the machine with its outer housing removed, in addition to the Airsep concentrator, machine 16 includes the motor 26 of peristaltic pump 14, an ionization box 28 and a flow control needle valve 30 which enables an operator to control the flow of oxygen generated by the concentrator and being conveyed to valve 30 via tubing 31 to the ionizer box 28 via tubing 32. The flow control needle valve 30 is manufactured by Ingersoll Rand of Montvale, N.J., part #104104-F02.

As shown in FIG. 4, ionization box 28 includes a chamber 34 which is the component in box 28 that is connected to tubing 32 and receives the oxygen generated by the concentrator. As also shown, chamber 34 includes needles 36 mounted therein which are supplied with high voltage power by an adjustable power supply 38 to ionize the oxygen. Needles 36 are standard steel sewing pins that have had their pin heads cutoff. They are inserted through the side of chamber 34, epoxied in place, wired together and wired to adjustable power supply 38 as shown in FIGS. 4 and 6.

Figure 6:
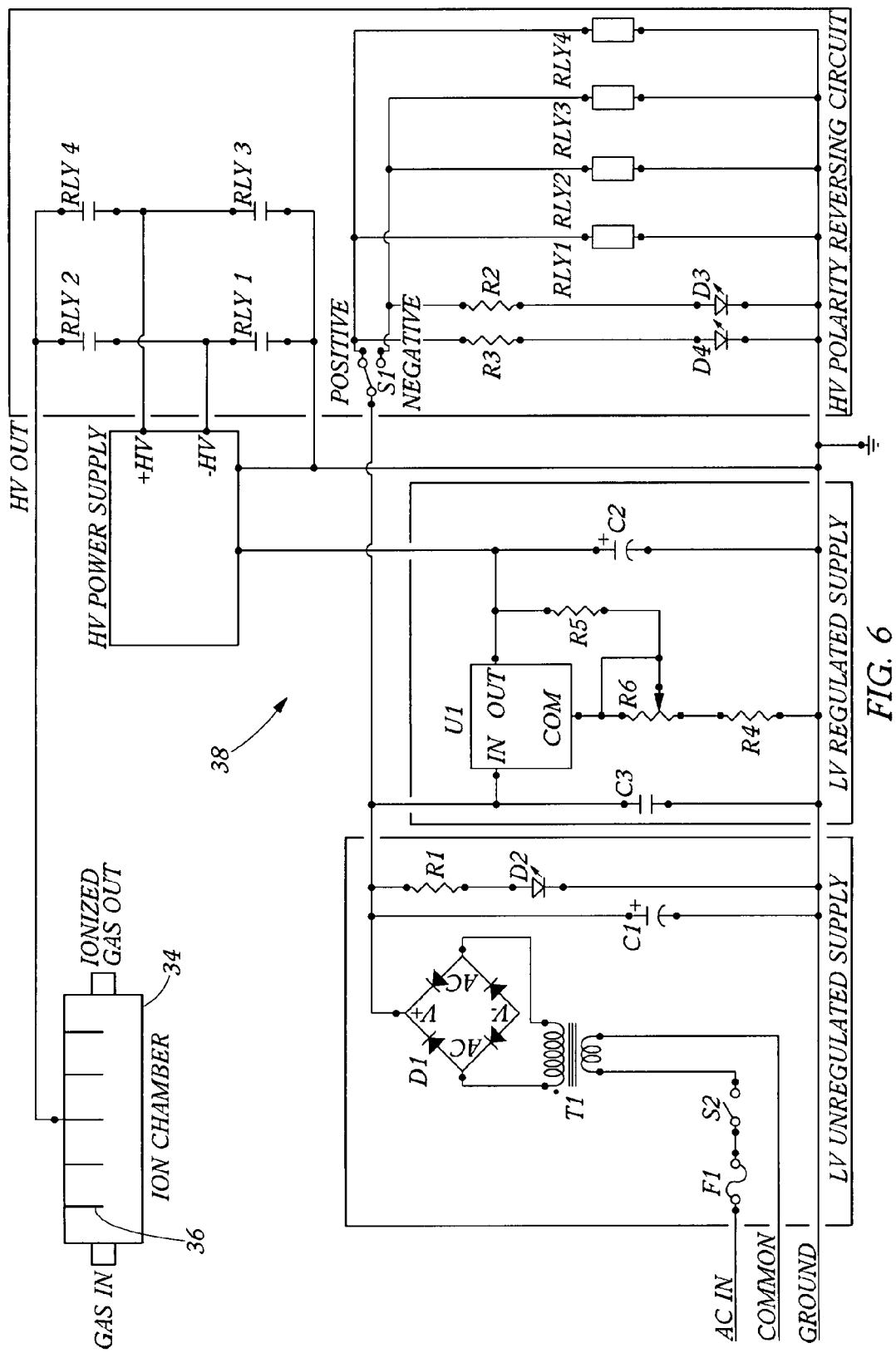
FIG. 6 is an electronic circuit schematic diagram of the ionization chamber and adjustable power supply referenced in FIG. 4.

Adjustable power supply 38 as shown in detail in the schematic of FIG. 6 consists of an unregulated low voltage source which applies power to a high voltage polarity selection circuit, and to an adjustable regulated low voltage source. The adjustable regulated voltage source, in turn, applies power to a high voltage converter. The unregulated low voltage source consists of a fuse F1; a power switch S2; a transformer T1; a bridge rectifier D1; and a filter capacitor C1. The adjustable low voltage power source consists of capacitors C2, and C3; an adjustable integrated circuit voltage regulator U1; and resistors R4, R5, and R6 which allow for adjustment of the output voltage. The regulated low voltage is then applied to a high voltage converter whose output polarity is selected by means of the polarity selection circuit consisting of switch S1 and relays RLY1, RLY2, RLY3, and RLY4. The resulting high voltage can thus be adjusted to control the amount and polarity of the charge imparted to the gas (oxygen). Typically, to effectively ionize the gas in chamber 34 the voltage imparted to chamber 34 by power supply 38 is at least 1000 volts.

As also shown in FIG. 6, light emitting diode (LED) D2 with resistor R1 act as a power on/off indicator 40 on the top panel 42 of machine 16 as shown in FIG. 2 which is switched between the on and off positions by a toggle switch 44. LED D3 identified by numeral 46 with resistor R2 and LED D4 identified by numeral 48 with resistor R3 indicate negative or positive polarity power output respectively. Toggle switch 50 is also provided on the panel 42 for switching the circuitry as described above to reverse the polarity of the charge imparted to the oxygen.

Returning to FIG. 4, it is also shown that chamber 34 is connected to tubing 24 which conveys the oxygen having been ionized in chamber 34 to the spray nozzle. As previously indicated, flow control needle valve 30 controls the flow of oxygen from the concentrator to chamber 34 and, as such, controls the flow of the ionized oxygen through the ionization chamber 34 to the spray nozzle. A knob 52 for flow control valve 30 is provided on the front panel 54 of machine 16 which when turned clockwise or counterclockwise enables one to control the flow of oxygen from 0 to 8 liters per minute. When 1 to 8 liters of oxygen per minute is pumped to spray nozzle 22 typically between about 1 and 10 ml per minute of saline solution is pumped to nozzle 22 by pump 14. An adjusting screw (not shown) on pump 14 enables control over the flow of saline solution pumped by pump 14.

Front panel 54 also includes on/off switches 56 and 58 for the peristaltic pump 14 and concentrator, respectively. Numeral 60 identifies an LCD meter for indicating the hours used by the concentrator and is part of the concentrator and provided by the concentrator manufacturer Airsep.

This invention has been described in detail with reference to particular embodiments thereof, but it will be understood that various other modifications can be effected within the spirit and scope of this invention. For example, the treatment could be modified as desired or perhaps even enhanced by adding a substance or substances to the saline solution.

We claim:

1. A skin treatment method comprising:
providing a mixing chamber;
providing substantially pure oxygen gas;
ionizing the oxygen gas to produce ionized oxygen gas;
delivering the ionized oxygen gas to the mixing chamber at a rate of between about 1 and 8 liters per minute;
providing saline solution;
pumping the saline solution into the mixing chamber at a rate of between about 1 and 10 ml per minute;
mixing the ionized oxygen gas with the saline solution in the mixing chamber to produce a mist of energized saline solution; and
applying the mist of energized saline solution to skin to treat the skin without traumatizing the skin.

2. A skin treatment method as claimed in claim 1 wherein the mist is applied with a handheld wand.

3. A skin treatment method as claimed in claim 1 further comprising adding a substance to the saline solution to modify the treatment process as desired.

4. A skin treatment method as claimed in claim 1 wherein the oxygen gas is ionized to provide it with a negative charge.

5. A skin treatment method as claimed in claim 1 wherein the oxygen gas is ionized to provide it with a positive charge.

6. A skin treatment method comprising:
providing a mixing chamber;
providing an ionization chamber having a high voltage power supply;
providing an oxygen concentrator for generating substantially pure oxygen gas;
generating substantially pure oxygen gas from the oxygen concentrator;
conveying the substantially pure oxygen gas to the ionization chamber;
imparting a high voltage in excess of 1000 volts to the substantially pure oxygen gas in the ionization chamber to ionize the substantially pure oxygen;
delivering the substantially pure ionized oxygen gas to the mixing chamber at a rate of between about 1 and 8 liters per minute;
providing saline solution;
pumping the saline solution into the mixing chamber at a rate of between about 1 and 10 ml per minute;
mixing the substantially pure ionized oxygen gas with the saline solution in the mixing chamber to produce a mist of energized saline solution; and applying the mist of energized saline solution to skin to treat the skin without traumatizing the skin.

* * * * *